United States Patent [19]

Alderman et al.

[11] Patent Number: 4,528,125

[45] Date of Patent: Jul. 9, 1985

[54] SUSTAINED RELEASE COMPOSITIONS

[75] Inventors: Daniel A. Alderman; Maurice L. Zweigle, both of Midland, Mich.

[73] Assignee: The Dow Chemical Company, Midland, Mich.

[21] Appl. No.: 471,595

[22] Filed: Mar. 3, 1983

[51] Int. Cl.³ ............................ A61K 7/46; C11B 9/00
[52] U.S. Cl. ................................................ 252/522 A
[58] Field of Search ................................... 252/522 A

[56] References Cited

U.S. PATENT DOCUMENTS

| | | | |
|---|---|---|---|
| 3,609,102 | 9/1971 | Schlossman | 252/522 A |
| 3,688,985 | 9/1972 | Engel | 252/522 A X |
| 3,691,271 | 9/1972 | Charle et al. | 252/522 A X |
| 3,767,787 | 10/1973 | Segal | 252/522 A X |
| 3,939,099 | 2/1976 | Tusa et al. | 252/522 A |
| 3,981,821 | 9/1976 | Kiritani et al. | 252/522 A X |
| 4,067,824 | 1/1978 | Teng et al. | 252/522 A |
| 4,128,507 | 12/1978 | Mitzner | 252/522 A |
| 4,428,869 | 1/1984 | Munteanu et al. | 252/522 A |

FOREIGN PATENT DOCUMENTS

| | | | |
|---|---|---|---|
| 54-55741 | 5/1979 | Japan | 252/522 A |
| 55-85515 | 6/1980 | Japan | 252/522 A |
| 55-81655 | 6/1980 | Japan | 252/522 A |
| 55-106159 | 8/1980 | Japan | 252/522 A |
| 58-143760 | 8/1983 | Japan | 252/522 A |

*Primary Examiner*—Helen M. S. Sneed

[57] ABSTRACT

Dispersions capable of the sustained release of active organic agents comprising an aqueous dispersion of a water-insoluble cellulose ether which cellulose ether particles have reversibly diffused therein the active agent. The dispersions may be used as dispersions, dewatered to form a powder, or coalesced to form films or other articles all of which are capable of sustained release of the active agent.

15 Claims, No Drawings

SUSTAINED RELEASE COMPOSITIONS

BACKGROUND OF THE INVENTION

This invention relates to compositions for the sustained release of flavorings or fragrances.

For many applications, it is desirable to provide a sustained release fragrance or flavoring composition. For example, volatile fragrances often exhibit a strong aroma for a relatively short period of time, but then exhibit little or no odor. An equivalent amount of such fragrance could be more effectively employed if small portions thereof were released into the atmosphere over a longer period of time.

Similarly, many flavorings, especially those employed in chewable substances such as chewing gums or chewing tobacco, are advantageously released in continuous, small amounts.

Various processes are known in which polymeric materials are employed in conjunction with flavorings or fragrances to form sustained release systems. For example, in U.S. Pat. Nos. 3,795,744 and 3,857,964, it is taught to form a coating of a polymeric material such as a cellulose ether around the flavoring or fragrance to be released therefrom. The flavoring or fragrance is released by the physical destruction of the polymeric coating or by the leaching of the flavoring or fragrance through the polymeric coating. Unfortunately, due to the limitations in size and physical form of such coated compositions, the use thereof is greatly restricted. In addition, the coating operation must be carefully controlled in order to obtain a product having predictable and desirable release characteristics.

Another conventionally employed sustained release system comprises forming a solid matrix of a binder material such as a cellulose ether, which matrix has dispersed therein the flavoring or fragrance to be released. While such matrix systems are somewhat useful in the preparation of pharmaceutical tablets, the size of such matrix systems often precludes the use thereof in other applications. In addition, the flavoring or fragrance is often unevenly distributed in such matrix systems, causing uneven release thereof.

Accordingly, an easily prepared sustained release system for flavorings or fragrances, which system has a physical form amenable to a variety of uses would be highly desired.

SUMMARY OF THE INVENTION

The present invention is an aqueous dispersion comprising a plurality of solid particles of a water-insoluble, organophilic cellulose ether, said particles having reversibly diffused therein a flavoring or fragrance which exhibits a greater affinity for the cellulose ether than for the aqueous phase. Under suitable conditions, the flavoring or fragrance diffuses out of the cellulose ether particles, thereby producing a continuous, sustained release of the flavoring or fragrance. The dispersions of this invention can be employed while in the form of a dispersion or may be dewatered using any suitable process to produce a powdery material having sustained release properties. In addition, the dispersions of this invention may be coalesced to form films or other articles which slowly release the flavoring or fragrance.

DETAILED DESCRIPTION OF THE INVENTION

The cellulose ether employed is one which is insoluble in water and one in which the flavoring or fragrance can become reversibly diffused. In general, the substituent groups on the cellulose ether are chosen such that it renders the cellulose ether somewhat organophilic. Exemplary cellulose ethers useful herein include the alkyl cellulose ethers, especially $C_2-C_4$ alkyl cellulose ethers; 2-hydroxyalkylcellulose ethers, especially $C_4$-hydroxyalkylcellulose ethers; mixed alkylhydroxyalkylcellulose ethers, especially $C_2-C_4$ alkyl $C_3-C_4$ hydroxyalkylcellulose ethers; and the like. In general, both the organophilic character and the water insolubility of these cellulose ethers increase with increasing size of the substituent alkyl or hydroxyalkyl groups, as well as with increasing amounts of such substitution. The manipulation of the amounts and types of substitution to prepare a water-insoluble product is within the skill of those familiar with preparing cellulose ethers, and an exhaustive enumeration of suitable cellulose ethers is not considered to be necessary herein. Most preferred are ethylcellulose ethylmethylcellulose, ethylhydroxypropylmethylcellulose such as described in U.S. Pat. No. 4,429,120, issued on Jan. 31, 1984, and the like.

The cellulose ether is dispersed as a plurality of finely divided particles into a continuous aqueous phase. Aqueous dispersion of water-insoluble cellulose ethers such as ethylcellulose and methods for their preparation are known in the art and are described, for example, in U.S. Pat. Nos. 2,345,879, 4,177,177 and in copending application Ser. No. 449,297, filed Dec. 13, 1982, and allowed on Oct. 10, 1984. At least sufficient water to form a continuous aqueous phase is employed, and more typically, sufficient water is employed to form a dispersion containing about 5–40 weight percent solids. The aqueous phase may contain, in addition to water, a comiscible or water-soluble organic compound or polymer, which may be present for purposes such as increasing or decreasing the viscosity of the aqueous phase, increasing the volatility thereof, increasing the compatibility thereof with additional, optional components of the dispersion, and the like. The use of such organic compound or polymer is beneficial as long as the flavoring or fragrance has a greater affinity for the cellulose ether particles than the aqueous phase. Examples of such organic compound or polymer include thickeners such as polyvinyl alcohol and water-soluble cellulose ethers; water-miscible organic compounds such as acetone, ethanol, methanol, and the like.

The cellulose ether is dispersed into the aqueous phase as a plurality of finely divided particles. While a suspending agent is not necessarily employed if the cellulose ether particles are sufficiently small or the viscosity of the aqueous phase sufficiently high, the preparation of such finely divided cellulose ether particles is difficult and a high viscosity aqueous phase is not generally desirable. Accordingly, a suspending agent is generally employed herein. In general, the choice of suspending agent is not especially critical as long as the dispersion is stabilized therewith, i.e., the dispersed particles do not substantially agglomerate or settle out of aqueous phase. However, the suspending agent must be chosen such that it is substantially inert to the flavoring or fragrance employed in the dispersion. For example, certain suspending agents, such as those containing weak acid groups, are primarily useful at high pH. Such suspending agents cannot be employed when the flavoring or fragrance is reactive or unstable at high pH. Similarly, suspending agents which are useful at low pH are not suitably employed when the flavoring or fragrance degrades or reacts at such low pH. Exemplary such stabilizers include surfactants, such as alkyl sulfonates and sulfates, alkyl benzyl sulfates and sulfonates, sulfonated condensation products of phenols or alkylphenols with ethylene oxide or propylene oxide, condensation products of long chain aliphatic alcohols with ethylene oxide, polymeric stabilizers such as polyvinyl alcohol, polyethylene glycol, carboxymethylcellulose or carboxymethylmethylcellulose and the like.

The suspending agent, when employed, is generally present in an amount from about 0.5–35 weight percent based on the weight of the dispersed polymer particles.

The dispersions of this invention further contain flavoring or fragrance which is reversibly diffused in the cellulose ether particles. Said flavoring or fragrance is an organic compound or composition which is capable of becoming reversibly diffused within the cellulose particle and which has a greater affinity for the cellulose ether than the aqueous phase. By "reversibly diffused in the cellulose ether particles" is meant that the flavoring or fragrance is associated with the cellulose ether particles in such a manner that under suitable conditions it can be released therefrom in its active form. The nature of the association of the flavoring or fragrance with the cellulose ether particles is not especially critical as long as it is reversible and may be, for example, an absorption, an adsorption, or a dissolution of the active agent into the cellulose ether particles.

Organic flavorings usefully employed herein include the so-called essential oils such as allspice, almond, anise, basil, bay, cardamon, cassia, cinnamon, cherry, clove, ginger, lemon, lime, nutmeg, orange, arrow root, pepper, peppermint, sage, spearmint, thyme, and wintergreen oils; plant extracts such as vanilla, licorice, coffee, tea, coconut, cherry bark, elm bark, and the like extracts; and artifical flavorings such as anethole, benzyl acetate, cinnamaldehyde, methyl anthranilate, methyl salicylate, citral, menthol, allyl caproate, ethyl methylphenylglycidate, vanillin, ethylbutyrate, diacetyl, eugenol, isoamyl acetate, and the like. Additional flavorings, natural and artificial, are described on pages 463–4 of Rogers and Fischelti, "Flavorings and Spices," *Encyclopedia of Chemical Technology,* 3rd Edition, Vol. 10, published by John Wiley & Sons (1980).

It is understood that the foregoing flavorings are generally employed in solutions in an organic solvent which is typically ethanol or an ethanol-water cosolvent. For the purposes of this invention, liquid flavorings may be employed neat, or as solutions, suspensions, or emulsions in any appropriate solvent, emulsion, or suspension medium. The particular form of the flavoring is not especially critical as long as it is capable of becoming reversibly diffused into the cellulose ether particles, and has greater affinity for cellulose ether particles than for the aqueous phase. Preferably, the flavoring is employed as a solution in alcohol or an alcohol/water cosolvent system.

Fragrances suitably employed herein include any of the commercial perfume and fragrance formulations. Alternatively, the so-called essential oils and the like which are commonly employed in scents, may be used herein. Suitable essential oils include amyris, bay, birch, beechwood, rosewood, camphor, cananga, eucalyptus, germanium, jasmine, labdanum, lavandin, lavender, lemon, lime, mint, neroli, origanum, orris root, patchouli, pine, rose, rosemary, sandalwood, ylang ylang, and the like. Additional fragrances include clove leaf oil, orange flower water, tuberose extract, floral aldehydric perfumes, benzoin, castoreum, civet, Maté mimosa, myrrh, oakmoss, violet leaves absolute, and the like. Artificial fragrances include the so-called aroma chemicals such as acetylated cedarwood terpenes, amylcinnamic aldehyde, amyl salicylate, benzyl acetate, benzyl salicylate, citronellol, coumarin, Galaxolide, hexylcinnamic aldehyde, isobornyl acetate, tinalool, Lyral, musk ambrette, phenethyl alcohol, tetrahydromuguol, and the like.

The foregoing fragrances may be employed herein neat, if liquids, or more preferably as solutions in organic solvents, i.e., as resinoids, concretes, absolutes or tinctures, or as present in commercial fragrance formulations. The particular form employed is not particularly critical as long as the fragrance is capable of becoming reversibly diffused into the cellulose ether particles and exhibits a greater affinity for the cellulose ether particles than for the aqueous phase.

Water-insoluble cellulose ethers are compatible with a wide range of the aforementioned flavorings or fragrances. Any such flavoring or fragrance, which is readily diffused into and retained by the cellulose ether particle, may be employed as the flavoring or fragrance herein. In addition, those flavorings or fragrances which have only limited compatibility with the cellulose ether, (i.e., those which are not readily diffused into the cellulose ether or which rapidly diffuse out of the cellulose ether), can be used herein if employed in conjunction with a compatibilizing material which increases the compatibility of the flavoring or fragrance and the cellulose ether. Said compatibilizing agent comprises an organic compound or polymer which is compatible with both the cellulose ether and the flavoring or fragrance, and which (a) enables the flavoring or fragrance to become more readily diffused into the cellulose ether particles, and/or (b) enables the flavoring or fragrance to diffuse out of the cellulose ether particles at a desirable rate under the conditions of use. For example, many essential oils may be desirably employed as the active agent herein, but are not sufficiently compatible with many cellulose ethers to be diffused into the cellulose ether particles in useful quantities. The small quantity of essential oil which becomes diffused into the cellulose ether particles rapidly diffuses back out. However, when dibutylphthalate or other compatibilizing material is employed, significant quantities of said essential oils can be diffused into the cellulose ether particles, and the rate of release of the diffused essential oil is significantly reduced.

Exemplary compatibilizing materials are described hereinafter. The particular choice of compatibilizing material employed, if any, will, of course, depend on the particular flavoring or fragrance employed. In general, compatibility of the flavoring or fragrance with the compatibilizing compound will be within the knowledge of the skilled artisan. Alternatively, the compatibility can often be established by routine experimentation, such as by simply mixing or blending the flavoring or fragrance and the compatibilizing material in the desired proportions to see if they form a homogeneous blend. Similarly, optimum amounts of compatibilizing materials employed can be established by simple experimentation. In general, however, said compatibilizing agent is advantageously employed in an amount in the range from about 0.5–50, preferably from about 5–30 weight percent based on the weight of the cellulose ether.

Materials suitably employed as a compatibilizing material include phosphate esters such as tri-(2-ethylhexyl)phosphate, tricresylphosphate and triphenylphosphate; phthalate esters such as benzylmethylphthalate, cyclohexylbutylphthalate, dibutylphthalate, dimethylphthalate, diphenylphthalate, diethoxyethylphthalate and the like; fatty acids, and salts and esters thereof; fatty alcohols; vegetable oils such as castor oil and corn oil; glycol esters of carboxylic acids, mineral oils, and the like. In addition, surfactants such as are described in U.S. Pat. No. 4,256,505 to Zweigle (hereinafter incorporated by reference) are also suitable compatibilizing materials. Many of the known plasticizers for water-insoluble cellulose ethers are also useful herein as a compatibilizing material.

Any amount of flavoring or fragrance may be employed in the dispersions of this invention as long as the flavoring or fragrance is diffused into the cellulose ether particles and a stable dispersion is maintained. It is understood that the maximum amount of flavoring or fragrance suitably employed will depend somewhat on the particular flavoring or fragrance cellulose ether and compatibilizing materials, if any, employed. In addition, the amount of flavoring or fragrance will depend somewhat on the amount thereof desirably released and the rate of release thereof by the cellulose ether particles. Thus, the amount of flavoring or fragrance may range, in general, from about 0.1 to about 200, preferably 5 to 100, more preferably 20 to 50, percent based on the weight of the cellulose ether.

In addition to the foregoing components, a dispersion of this invention may, optionally, contain other ingredients as are commonly employed in polymeric dispersions including, for example, flavorings, preservatives, pigments, fillers and the like. For certain uses, such as when the dispersions of this invention are to be formed into films or molded articles, it may be desirable to employ a plasticizer in the dispersion in order to improve the mechanical properties of the cellulose ether. Plasticizers for cellulose ethers are well known and include, for example, esters of phthalic acid, phosphate esters, fatty acids and salts and esters thereof, and the like. It is noted that such plasticizers are often useful as compatibilizing materials as well as to improve the mechanical properties of the cellulose ether. Salts of fatty acids, particularly ammonium salts thereof, are of particular interest because such salts perform the three-fold function of plasticizing the cellulose ether, compatibilizing the active agent with the cellulose ether and stabilizing the dispersion. Because of the need to maintain an alkaline pH in dispersions employing fatty acid salts as stabilizers, however, such fatty acid salt-stabilized dispersions are generally not preferred when the active agent degrades or reacts in an alkaline medium.

In addition to the foregoing optional ingredients, the water-insoluble ether may be employed in conjunction with one or more other polymeric materials which may be employed for their particular beneficial properties. Said other polymers may be any which is compatible with, i.e., miscible with or soluble in the water-insoluble cellulose ether, including water-soluble cellulose ethers, such as methylcellulose, hydroxypropylcellulose, hydroxypropylmethylcellulose, carboxymethylhydroxyethylcellulose, polyacrylamides, polyacetates, diverse cellulose esters, and the like.

The dispersions of this invention are advantageously prepared by the simple mixing of the flavoring or fragrance into the previously prepared dispersion of the water-insoluble, organophilic cellulose ether. The amount of flavoring or fragrance employed in preparing the dispersions of this invention is that amount which is desirably diffused into the cellulose ether particles. Upon mixing the flavoring or fragrance with the cellulose dispersion, agitation for a relatively short period, typically about five minutes to six hours, usually is effective to cause the diffusion of the active agent into the cellulose ether particles. Often, mild heating (i.e., to a temperature of about 30°–80° C.) of the cellulose ether dispersion is desirable or necessary during the mixing of the flavoring or fragrance into the dispersion in order to obtain adequate diffusion of the flavoring or fragrance into the cellulose ether particles.

Once prepared, the dispersions of this invention may be employed in any desirable manner. For example, the dispersion may be sprayed or otherwise applied to the system to be treated with the flavoring or fragrance, or may be incorporated with other ingredients (for example, a chewing gum base) to form a final product containing the active agent. Alternatively, the dispersion can be dewatered such as by centrifugation or spray drying to form a powder having sustained release properties. In addition, the cellulose ether particles may be coalesced using methods known in the art to form films or other articles having sustained release properties. The sustained release dispersions of this invention possess several advantages over conventional sustained release systems. The flavoring or fragrance is readily diffused into the cellulose ether particles. In contrast to matrix type sustained release systems, the flavoring or fragrance is more uniformly distributed throughout the cellulose ether particles. The physical form of the dispersion of this invention allows for a wide variety of uses not available to conventional sustained release systems. In addition, the compositions of the dispersion of this invention are readily adapted to tailor the dispersion for the desired end use.

The dispersions of this invention may be employed as a sustained release flavoring agent in various forms. The dispersions may be directly formulated into the compositions to be flavored therewith. Alternatively, the dispersions may be dewatered by any suitable means and the resulting sustained release flavored particles dispersed into the composition to be flavored. The flavored particles may also be compressed into a flavored tablet, if desired. In addition, the dispersions of this invention may be formed into flavored coatings for drugs, vitamins, capsules, gums, candies, lozenges and the like.

Another exemplary use for the dispersions of this invention is as a sustained release fragrance, such as in perfumes, colognes, deodorants, scents, room fresheners, soaps, other cosmetics and household goods and the like. Here again, the form of use of the dispersion of this invention is a matter of choice and convenience to the practioner in the art.

The following examples are provided to illustrate the scope of the invention but not to limit the scope thereof. All parts and percentages are by weight unless otherwise indicated.

EXAMPLE 1

In this example, a 30 percent solids aqueous dispersion containing particles containing 75 weight percent ethylcellulose and 25 weight percent oleic acid is employed. The pH of the aqueous phase is adjusted to about 9–10 with ammonia. To 100 g of the ethylcellulose dispersion is added 25 g of lemon oil, USP. The mixture is heated to 70° C. and stirred at that temperature for 10 minutes. The resulting dispersion is then cooled. A portion of the resulting dispersion is cast as a film on a sheet of glass and dried at 140° F. This film has a strong lemon aroma which remains strong for 2 days and is still detectable after standing at room temperature for 6 days. A faint lemon flavor is noticed upon placing a portion of the newly-dried film in one's mouth. The flavor becomes strong on chewing the film. The flavor is still detectable after the film has been standing 6 days at room temperature.

EXAMPLE 2

A 100-g portion of the ethylcellulose dispersion employed in Example 2 is mixed with 50 g of Avon Everest brand cologne. The mixture is stirred for about 30 minutes at 75° C. A portion of the resulting dispersion is then cast onto paper. For comparison, a sample of Avon cologne as sold commercially is placed onto a separate sheet of paper. After 6 hours, the paper containing the dispersion of this invention had a noticeably stronger aroma than the control sample. After 3 days, the sample of this invention still exhibited a noticeable odor. The control exhibited little or no odor after 6 hours.

EXAMPLE 3

To a 100-g portion of Aquacoat* ethylcellulose dispersion is added 50 percent based on weight of the solids of Aquacoat and 25 weight percent based on solids of oleic acid. This mixture was heated at 75° C. for 30 minutes. The resulting flavor dispersion is cast as a film on glass and dried at room temperature until the water is evaporated. The resulting film exhibited a sustained flavor and fragrance. This experiment is repeated without adding oleic acid. Without oleic acid, the cherry oil did not diffuse into the Aquacoat.
* Trademark of FMC Corporation

What is claimed is:

1. An aqueous dispersion capable of a sustained release of a fragrance, said dispersion comprising a plurality of particles of a water-insoluble, organophilic cellulose ether dispersed into an aqueous phase, said cellulose ether having reversibly diffused therein an organic fragrance which fragrance exhibits a greater affinity for the cellulose ether than for the aqueous phase.

2. The dispersion of claim 1 wherein the cellulose ether is ethylcellulose or ethylhydroxypropylmethylcellulose.

3. The dispersion of claim 1 wherein the fragrance comprises an essential oil, a plant extract, or an aroma chemical.

4. The dispersion of claim 1 further comprising a compatibilizing material which increases the compatibility of the fragrance and the cellulose ether.

5. The dispersion of claim 4 wherein the compatibilizing material comprises a fatty acid or salt or ester thereof; phthallic acid or esters thereof; a fatty alcohol; a phosphate ester; or a glycol ester of a carboxylic acid.

6. The dispersion of claim 5 wherein the fragrance comprises an essential oil, a plant extract, or an aroma chemical.

7. The dispersion of claim 6 wherein the compatibilizing material is dibutylphthalate or a fatty acid or salt thereof.

8. The dispersion of claim 7 wherein the cellulose ether is ethylcellulose or ethylhydroxypropylmethylcellulose.

9. The dispersion of claim 1 wherein the aqueous dispersion comprises particles of ethylcellulose or ethylhydroxypropylmethylcellulose, which particles are plasticized with a plasticizing composition comprising a carboxylic acid which is a plasticizer for said cellulose ether, and the aqueous phase has a pH sufficiently high that sufficient of the carboxylic acid is in salt form to stabilize the dispersion.

10. The dispersion of claim 9 wherein the carboxylic acid is a fatty acid.

11. The dispersion of claim 10 wherein the fragrance comprises an essential oil, a plant extract, or an aroma chemical.

12. A powder containing an organic fragrance, which powder is formed by dewatering of the dispersion of claim 1.

13. A powder containing an organic fragrance, which powder is formed by dewatering of the dispersion of claim 9.

14. A film or other article containing the organic fragance, which film or other article is formed by the coalescence of the dispersion of claim 1.

15. A film or other article containing the organic fragrance, which film or other article is formed by the coalescence of the dispersion of claim 9.

* * * * *